United States Patent [19]

Ikura et al.

[11] Patent Number: 5,977,370

[45] Date of Patent: Nov. 2, 1999

[54] PROCESS FOR PREPARING PYRIDINE CHLORIDE

[75] Inventors: Kiyoshi Ikura; Nobuhiro Katsumata, both of Arai, Japan

[73] Assignee: Daicel Chemical Industries, Ltd., Osaka, Japan

[21] Appl. No.: 09/209,720

[22] Filed: Dec. 11, 1998

[51] Int. Cl.⁶ .................................................. C07D 213/61
[52] U.S. Cl. ............................................................ 546/345
[58] Field of Search ................................................ 546/345

[56] References Cited

U.S. PATENT DOCUMENTS 4,127,575  11/1978  McGregor ................................ 546/345
4,172,203  10/1979  Ison ......................................... 546/345
4,515,953   5/1985  Marinak et al. ........................ 546/345

FOREIGN PATENT DOCUMENTS 58-206564  12/1983  Japan .
61-249965  11/1986  Japan .
 3-200769   9/1991  Japan .
 5-339235  12/1993  Japan .
  1215387  12/1970  United Kingdom .
WO 98/50362  11/1998  WIPO .

*Primary Examiner*—Patricia L. Morris
*Attorney, Agent, or Firm*—Marshall, O'Toole, Gerstein, Murray & Borun

[57] ABSTRACT

An improved method of preparing a pyridine chloride from a chlorohydrazinopyridine is disclosed.

6 Claims, No Drawings

PROCESS FOR PREPARING PYRIDINE CHLORIDE

FIELD OF THE INVENTION

The present invention relates to a process for preparing a pyridine chloride, which are useful intermediates in pesticide and drug manufacturing.

DESCRIPTION OF THE RELATED ART

Heretofore, various processes for preparing a pyridine chloride have been suggested.

For example, Japanese Patent Kokai Publication No. 249965/1986 discloses a process for preparing a pyridine chloride, which comprises a liquid phase chlorination of a pyridine or pyridine hydrochloride. However, according to this process, various pyridine chlorides are formed. Therefore, a complicated isolation step is required, and it is difficult to isolate a specific pyridine chloride.

Japanese Patent Kokai Publication No. 206564/1983 discloses a process for preparing a pyridine chloride, which comprises utilizing a gas phase chlorination method to chlorinate pyridine. However, because this process relies on a gas phase reaction, the reaction step is complicated and, similar to the liquid phase chlorination method described above, various pyridine chlorides are formed.

Great Britain Patent No. 1215387 discloses a process for preparing 2,3,5-trichloropyridine, which comprises chlorination of 2-amino-3,5-dichloropyridine as a starting material. However, according to this process, the starting material is expensive and, therefore, this process has a disadvantage with respect to manufacturing costs.

U.S. Pat. No. 4,127,575 discloses a process for preparing 2,3,5-trichloropyridine, which comprises oxidizing 2,3,5-trichloro-6-hydrazinopyridine or 2,3,5-trichloro-4-hydrazinopyridine with sodium hypochlorite in a solvent. This process is superior with respect to selectively providing the desired product. However, according to this process, because a large amount of a solvent, such as toluene, is used, and because sodium hypochlorite is supplied in the form of an aqueous solution having a concentration of about 15%, the so-called space-time yield is very low. Moreover, according to this process, a large amount of sodium hypochlorite having a high unit cost is used. In addition, because an inexpensive reaction vessel made of a stainless steel is corroded by sodium hypochlorite, an expensive reaction vessel is required. Therefore, manufacturing costs are increased.

As a process for preparing a pyridine chloride to solve these disadvantages, Japanese Patent Kokai Publication No. 200769/1991 discloses a process for preparing a pyridine chloride, which comprises oxidizing 2,3,5-trichloro-6-hydrazinopyridine, 3,6-dichloro-2-hydrazinopyridine, or 3,5-dichloro-2-hydrazinopyridine with hydrogen peroxide in a solvent, then extracting with an organic solvent, followed by concentration and fractionation. By employing this process, the yield of pyridine chloride can be enhanced to some extent, thereby making it possible to reduce manufacturing costs.

However, when this process for preparing a pyridine chloride, which comprises oxidizing with hydrogen hypochlorite, is scaled up to an industrial level, separation between the water and an organic solvent becomes poor. The cause of this poor separation is not known in detail, but it is theorized that poor phase separation is caused by the formation of tar by-products. This is a problem because the yield of a pyridine chloride is decreased by this poor phase separation. An additional problem is that the production sequence is complicated by utilizing a countermeasure to overcome the poor phase separation. Therefore, it becomes impossible to sufficiently reduce the manufacturing costs of a pyridine chloride. Accordingly, a development of a process capable of preparing a pyridine chloride in a higher yield at a lower cost in an industrial production sequence is presently required.

SUMMARY OF THE INVENTION

The present invention has been accomplished to solve these problems. Therefore, an aspect of the present invention is to provide a process capable of preparing a pyridine chloride in a high yield at a low cost.

The invention accomplished to solve the above problems provides a process for preparing a pyridine chloride comprising a reaction step of oxidizing (a) a chlorohydrazinopyridine starting material, represented by the following general formula (1):

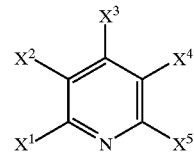

wherein $X^1$ to $X^5$ are the same or different, and represent a chlorine atom, a hydrogen atom, or a hydrazino group (—$NHNH_2$), provided that at least one of $X^1$ to $X^5$ represents a chlorine atom and at least one of $X^1$ to $X^5$ represents a hydrazino group, with (b) hydrogen peroxide, in the presence of (c) a phase transfer catalyst in (d) a mixed solvent of an organic solvent and water.

According to the present invention, because a chlorohydrazinopyridine is oxidized with hydrogen peroxide in the presence of a phase transfer catalyst in a mixed solvent of an organic solvent and water, poor phase separation between water and the organic solvent does not occur after the completion of the reaction. Accordingly, a pyridine chloride can be obtained in a high yield. Moreover, since a countermeasure to overcome the poor phase separation, which complicates the production, is not required, the manufacturing costs of a pyridine chloride can be reduced.

In the present invention, a mixing ratio of the organic solvent to water in the mixed solvent preferably is from 1/100 to 100/1, in terms of a weight ratio, and the amount of mixed solvent used preferably is from 10 to 1000 parts by weight, based on 100 parts by weight of the chlorohydrazinopyridine. Consequently, the phase separation properties after the formation of a pyridine chloride can be improved, thereby making it possible to reduce the production costs of a pyridine chloride.

Furthermore, in the present invention, the amount of the phase transfer catalyst used is preferably from 0.01 to 100 parts by weight, based on 100 parts by weight of the chlorohydrazinopyridine. Consequently, the yield of a pyridine chloride can be further increased.

In these inventions, if a basic compound is added to the reaction system in the reaction step, the reaction to form a pyridine chloride is promoted, thereby making it possible to obtain a pyridine chloride in a high efficiency.

This invention is particularly effective when a trichloropyridine is prepared using a trichlorohydrazinopyridine.

DESCRIPTION OF THE PREFERRED EMBODIMENTS

In the process of the present invention, a chlorohydrazinopyridine represented by the above chemical formula (1) is used as a starting material. The chlorohydrazinopyridine is oxidized with hydrogen peroxide to substitute a hydrazino group with a hydrogen atom, thereby obtaining a pyridine chloride. When the chlorohydrazinopyridine starting material is monochlorohydrazinopyridine, monochloropyridine can be obtained. When the chlorohydrazinopyridine starting material is a dichlorohydrazinopyridine, a dichloropyridine can be obtained. When it is a trichlorohydrazinopyridine, a trichloropyridine can be obtained. When it is tetrachlorohydrazinopyridine, tetrachloropyridine can be obtained. Thus, a specific pyridine chloride can be formed by selection of the starting material, and the selectivity of the product can be enhanced.

A chlorohydrazinopyridine starting material can be obtained by a known method. A chlorohydrazinopyridine can be obtained, for example, by selectively substituting a chlorine atom positioned in a predetermined position of an existing pyridine chloride with a hydrazino group. The pyridine chloride obtained by substituting a hydrazino group of this chlorohydrazinopyridine with a hydrogen atom corresponds to that pyridine chloride obtained by selectively substituting a chlorine atom situated at the predetermined position of an existing pyridine chloride with a hydrogen atom. Therefore, the number of chlorine atoms present in the resulting pyridine chloride is smaller than that of an existing pyridine chloride. For example, tetrachloropyridine can be obtained from pentachloropyridine via tetrachlorohydrazinopyridine, a trichloropyridine can be obtained from a tetrachloropyridine via a trichlorohydrazinopyridine, and a dichloropyridine can be obtained from a trichloropyridine via a dichlorohydrazinopyridine. In such way, the process for preparing a chlorohydrazinopyridine by selectively substituting a chlorine atom situated at the position of existing pyridine chloride with a hydrazino group includes, for example, a process of reacting an existing pyridine chloride with hydrazine hydrate, particularly a process of controlling the equivalent number of hydrazine hydrate (see Japanese Patent Kokai Publication No. 339235/1993, *J. Chem. Soc.*, (c) 167, published in 1971).

The oxidizing reaction using hydrogen peroxide is conducted in a solvent obtained by mixing an organic solvent with water, thereby preventing poor phase separation after completion of the pyridine chloride formation reaction. As the organic solvent, for example, an organic solvent which is insoluble, practically insoluble, or slightly soluble in water, is suitably used. An organic solvent suitably used in the present invention includes, for example, pentane, hexane, heptane, octane, benzene, toluene, xylene, mesitylene, or ethylbenzene.

A mixing ratio of organic solvent to water in the mixed solvent preferably is from 1/100 to 100/1, and particularly from 1/10 to 10/1. When the mixing ratio is smaller than the above range, the yield of pyridine chloride is sometimes lowered. On the other hand, when the mixing ratio exceeds the above range, the reaction rate is sometimes decreased, and the yield of pyridine chloride is sometimes lowered.

The amount of mixed solvent used preferably is not less than 10 parts by weight, and particularly not less than 50 parts by weight, based on 100 parts by weight of the chlorohydrazinopyridine. When the amount of mixed solvent is smaller than the above range, the yield of pyridine chloride is sometimes lowered. No problems arise even if the amount of mixed solvent is large. However, the amount preferably is not more than 1000 parts by weight, and practically not more than 500 parts by weight, based on 100 parts by weight chlorohydrazinopyridine, taking the prevention of a reduction in spacetime yield into consideration.

In the present invention, a chlorohydrazinopyridine is oxidized with hydrogen peroxide in the presence of a phase transfer catalyst, thereby making it possible to increase the yield of the pyridine chloride. The term "phase transfer catalyst" used herein means all substances, which promote transfer of ions, charged molecules, and neutral molecules existing in each phase to the other phase in a solvent forming two phases which are heterogeneous each other, and includes, for example, quaternary ammonium salt, phosphonium salt, amine, crown ether, and cryptand.

The phase transfer catalyst used suitably in the present invention includes, for example, tetraethylammonium chloride, tetraethylammonium bromide, tetrabutylammonium chloride, tetrabutylammonium hydrogen sulfate, tetrabutylammonium bromide, tetrabutylammonium iodide, tetrabutylammonium hydroxide, tetraoctylammonium chloride, tributylbenzylammonium chloride, tributylbenzylammonium bromide, trioctylbenzyl ammonium chloride, benzyltriethylammonium chloride, cetyldimethylbenzylammonium chloride, tributylbenzyl ammonium chloride, benzyltrimethyl ammonium chloride, tetrabutylphosphonium chloride, tetrabutylphosphonium bromide, trioctylethylphosphonium bromide, tetraphenylphosphonium bromide, trimethylamine, triethylamine, tributylamine, trioctylamine, tribenzylamine, 18-crown-6, dicyclohexyl-18-crown-6, and [2,2,2]-cryptate. Particularly suitable phase transfer catalysts include benzyltriethylammonium chloride and cetyldimethylbenzylammonium chloride.

The amount of the phase transfer catalyst used preferably is not less than 0.01 parts by weight, and particularly not less than 0.1 parts by weight, based on 100 parts by weight of chlorohydrazinopyridine. When the amount of the phase transfer catalyst is smaller than the above range, the reaction rate is sometimes lowered and the yield of pyridine chloride is sometimes lowered. No problems arise if the amount of the phase transfer catalyst is large. However, the amount preferably is not more than 100 parts by weight, and practically not more than 10 parts by weight, based on 100 parts by weight chlorohydrazinopyridine, taking the prevention of an increase in manufacturing cost into consideration.

In the present invention, a basic substance preferably is added to the reaction. By adding the basic substance, hydrazine hydrate is activated, thereby enhancing the formation efficiency of the pyridine chloride. The basic substance can be an inorganic or organic base, but preferably is an inorganic base because the purification step is simplified. Preferred inorganic bases include, for example, sodium hydrogen carbonate, sodium hydroxide, potassium hydroxide, sodium carbonate, potassium carbonate, and potassium hydrogen carbonate. Sodium hydrogen carbonate is particularly preferred.

The amount of the basic substance added varies depending on the amount of aqueous solvent, but preferably is from 1 to 1000 parts by weight, and particularly from 50 to 200 parts by weight, based on 100 parts by weight of chlorohydrazinopyridine. When the amount of the basic substance is smaller than the above range, the yield of pyridine chloride is sometimes lowered. To the contrary, when the amount of the basic substance exceeds the above range, the purification step sometimes becomes complicated.

It is necessary that the molar amount of hydrogen peroxide used in the present invention is the same as, or larger than, that of the chlorohydrazinopyridine. A 1–3 equimolar amount of hydrogen peroxide usually is used. The oxidizing reaction using hydrogen peroxide usually is conducted over 1 to 20 hours. The reaction usually is conducted at 0 to 200°

C., and preferably at 50 to 100° C. Hydrogen peroxide is charged in the reaction system in the form of aqueous hydrogen peroxide. Aqueous hydrogen peroxide can be charged at one time, but is usually added dropwise over about 1 to 15 hours.

After the completion of the reaction, the organic layer is separated, and the organic layer is concentrated by fractional distillation to obtain the pyridine chloride.

EXAMPLES

The following Examples further illustrate the present invention in detail but are not to be construed to limit the scope thereof.

Example 1

50 kg (kilograms) of 2,3,5-trichloro-6-hydrazinopyridine starting material, 45 kg of toluene as an organic solvent, 100 kg of water, 50 kg of sodium hydrogen carbonate as a basic substance, and 3 kg of benzyltriethylammonium chloride as a phase transfer catalyst were charged in order to a reaction vessel. The resulting reaction mixture was heated to 75° C., and 27 kg of aqueous 35% hydrogen peroxide was added dropwise to the reaction vessel over 10 hours.

After the completion of the reaction, the reaction mixture was allowed to stand for about 30 minutes, and then observed visually. As a result, the interface between the organic layer and aqueous layer was clear, and phase separation was good. The organic layer was concentrated by fractional distillation to obtain 2,3,5-trichloropyridine. The yield of 2,3,5-trichloropyridine was calculated based on 2,3,5-trichloro-6-hydrazinopyridine. As a result, the yield was 93%.

Example 2

According to the same method described in Example 1, except for adding 3 kg of cetyldimethylbenzylammonium chloride in place of benzyltriethylammonium chloride as the phase transfer catalyst, the oxidizing reaction using hydrogen oxide was conducted.

After completion of the reaction, the reaction mixture was allowed to stand for about 30 minutes, and then observed visually. As a result, the interface between the organic layer and aqueous layer was clear and the phase separation was good. The organic layer was concentrated by fractional distillation to obtain 2,3,5-trichloropyridine. The yield of 2,3,5-trichloropyridine was calculated based on 2,3,5-trichloro-6-hydrazinopyridine. As a result, the yield was 95%.

Comparative Example 1

50 kg of 2,3,5-trichloro-6-hydrazinopyridine starting material, 100 kg of water, and 65 kg of an aqueous 25% sodium hydroxide solution as a basic substance were charged in order to a reaction vessel. The reaction mixture was heated to 75° C., and 27 kg of aqueous 35% hydrogen peroxide was added dropwise to the reaction vessel over 10 hours. After the completion of the reaction, 45 kg of toluene was charged.

The reaction solution was allowed to stand for about 120 minutes, and then observed visually. As a result, a scum-like substance was present at the interface between the organic layer and aqueous layer. The scum-like substance was surrounded by both layers. Therefore, phase separation was poor. The organic layer was concentrated by fractional distillation to obtain 2,3,5-trichloropyridine. The yield of 2,3,5-trichloropyridine was calculated based on 2,3,5-trichloro-6-hydrazinopyridine. As a result, the yield was 84%.

Comparative Example 2

According to the same method as described in Example 1, except for adding no benzyltri-ethylammonium chloride, the oxidizing reaction using hydrogen peroxide was conducted.

The reaction solution was allowed to stand for about 120 minutes and then observed visually. As a result, a scum-like substance was present at the interface between the organic layer and aqueous layer. The scum-like substance was surrounded by both layers. Therefore, the phase separation was poor. The organic layer was concentrated by fractional distillation to obtain 2,3,5-trichloropyridine. The yield of 2,3,5-trichloropyridine was calculated based on 2,3,5-trichloro-6-hydrazinopyridine. As a result, the yield was 23%.

The above results are shown in Table 1 below.

|  | Example 1 | Example 2 | Comp. Example 1 | Comp. Example 2 |
| --- | --- | --- | --- | --- |
| Solvent | Toluene/water | Toluene/water | Water | Toluene/water |
| Phase transfer catalyst | Benzyltriethylammonium chloride | Cetyldimethylbenzylammonium chloride |  |  |
| Basic substance | Sodium hydrogen carbonate | Sodium hydrogen carbonate | Sodium hydroxide | Sodium hydrogen carbonate |
| Phase separation | Good | Good | Poor | Poor |
| Yield (%) | 93 | 95 | 84 | 23 |

As is apparent from Table 1, the processes of Example 1 and Example 2, wherein a chlorohydrazinopyridine is oxidized in the presence of a phase transfer catalyst in a mixed solvent of an organic solvent and water, is superior in phase separation properties and yield over the process of Comparative Example 1 (using no phase transfer catalyst in a solvent of water alone), and over the process of Comparative Example 2 (using no phase transfer catalyst). The superiority of the process of the present invention is proved by these test results.

As described above, the present invention provides a process for preparing a pyridine chloride, which can yield the desired product in a high yield, and requires no countermeasure to overcome a poor phase separation because of good phase separation properties, thereby making it possible to obtain the desired product at a low cost.

Since this process is superior in selectively providing the desired product, various pyridine chloride by-products are not formed. Therefore, it is not necessary to practice a step of isolating a specific pyridine chloride.

What is claimed is:

1. A process for preparing a pyridine chloride comprising the reaction step of oxidizing (a) a chlorohydrazinopyridine represented by the following general formula:

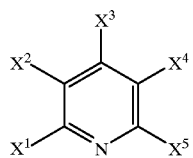

wherein $X^1$ to $X^5$ are the same or different, and represent a chlorine atom, a hydrogen atom, or a hydrazino group, provided that at least one of $X^1$ to $X^5$ represents a chlorine atom and at least one of $X^1$ to $X^5$ represents a hydrazino group, with (b) hydrogen peroxide, in the presence of a phase transfer catalyst in a mixed solvent of an organic solvent and water.

2. The process of claim 1 wherein a weight ratio of the organic solvent to the water in the mixed solvent is from 1/10 to 100/1.

3. The process of claim 1 wherein the amount of the mixed solvent is from 10 to 1000 parts by weight, based on 100 parts by weight of the chlorohydrazinopyridine.

4. The process of claim 1 wherein the amount of the phase transfer catalyst is from 0.01 to 100 parts by weight, based on 100 parts by weight of the chlorohydrazinopyridine.

5. The process of claim 1 wherein a basic compound is present in the reaction step.

6. The process of claim 1 wherein the chlorohydrazinopyridine is a trichlorohydrazinopyridine and the pyridine chloride is a trichloropyridine.

* * * * *